(12) United States Patent
   Spevak

(10) Patent No.: US 10,288,658 B2
(45) Date of Patent: May 14, 2019

(54) ENHANCING SENSITIVITY AND ROBUSTNESS OF MECHANICAL ROTATION AND POSITION DETECTION WITH CAPACITIVE SENSORS

(71) Applicant: Texas Instruments Incorporated, Dallas, TX (US)

(72) Inventor: Peter Spevak, Moosburg a.d. Isar (DE)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 15/886,173

(22) Filed: Feb. 1, 2018

(65) Prior Publication Data

US 2018/0217190 A1   Aug. 2, 2018

Related U.S. Application Data

(60) Provisional application No. 62/453,575, filed on Feb. 2, 2017.

(51) Int. Cl.
| G01R 27/26 | (2006.01) |
| G01N 27/22 | (2006.01) |
| G01N 27/24 | (2006.01) |
| G06F 3/038 | (2013.01) |
| G06F 3/0362 | (2013.01) |

(Continued)

(52) U.S. Cl.
   CPC ....... G01R 27/2605 (2013.01); G01D 5/2405 (2013.01); G01D 5/2412 (2013.01); G01D 5/2415 (2013.01); G01N 27/228 (2013.01); G01N 27/24 (2013.01); G06F 3/0362 (2013.01); G06F 3/0383 (2013.01);

(Continued)

(58) Field of Classification Search
   CPC ... G01D 5/2405; G01D 5/2412; G01R 31/028
   See application file for complete search history.

(56) References Cited

U.S. PATENT DOCUMENTS

2008/0087085 A1*  4/2008  Ueda ................... G01P 15/0891
                                                     73/514.32
2014/0118639 A1   5/2014  Matsushima
(Continued)

FOREIGN PATENT DOCUMENTS

| RU | 2507563 C1 | 2/2014 |
| WO | WO2010014356 A2 | 2/2010 |
| WO | WO2012047052 A2 | 4/2012 |

OTHER PUBLICATIONS

International Search Report and Written Opinion in PCT/US2018/016699, dated Jun. 7, 2018 (7 pages).

*Primary Examiner* — Giovanni Astacio-Oquendo
*Assistant Examiner* — Alvaro E Fortich
(74) *Attorney, Agent, or Firm* — Michelle F. Murray; Charles A. Brill; Frank D. Cimino

(57) ABSTRACT

Described example user interface control apparatus includes a first structure, with a first side, conductive capacitor plate structures spaced along a first direction on the first side, a movable second structure with an auxiliary conductive structure, and an interface circuit to provide excitation signals to, and receive sense signals from, the conductive capacitor plate structures to perform a mutual capacitance test and a self-capacitance test of individual ones of the conductive capacitor plate structures to determine a position of the second structure or a user's finger relative to the first structure along the first direction.

20 Claims, 15 Drawing Sheets

(51) Int. Cl.
  *G01D 5/24*       (2006.01)
  *G01D 5/241*      (2006.01)
  *G01R 31/02*          (2006.01)
  *G06F 3/041*          (2006.01)
  *G01R 31/28*          (2006.01)

(52) U.S. Cl.
  CPC ........ *G01R 31/028* (2013.01); *G01R 31/2829* (2013.01); *G06F 3/0416* (2013.01); *G09G 2320/029* (2013.01)

(56)       References Cited

U.S. PATENT DOCUMENTS

| | | |
|---|---|---|
| 2014/0267039 A1 | 9/2014 | Curtis |
| 2014/0292356 A1 | 10/2014 | Spevak |
| 2015/0346864 A1* | 12/2015 | Yang ....................... G06F 3/044 |
| | | 345/174 |
| 2015/0370388 A1 | 12/2015 | Choi et al. |
| 2016/0006449 A1 | 1/2016 | Spevak |
| 2016/0077630 A1 | 3/2016 | Inai |
| 2016/0220176 A1 | 8/2016 | Desnerck |
| 2016/0321810 A1 | 11/2016 | Lee |
| 2016/0364068 A1* | 12/2016 | Cheng ................... G06F 3/0416 |

\* cited by examiner

| CT1-1 | == | CAP1.3 + CAP0.0 + CAP2.0 | = | 12 + 1 + 2 |
|---|---|---|---|---|
| CT1-2 | == | CAP0.0 + CAP2.0 + CAP1.1 | = | 1 + 2 + 3 |
| CT1-3 | == | CAP2.0 + CAP1.1 + CAP3.1 | = | 2 + 3 + 4 |
| CT1-4 | == | CAP1.1 + CAP3.1 + CAP0.2 | = | 3 + 4 + 5 |
| CT1-5 | == | CAP3.1 + CAP0.2 + CAP2.2 | = | 4 + 5 + 6 |
| CT1-6 | == | CAP0.2 + CAP2.2 + CAP1.1 | = | 5 + 6 + 3 |
| CT1-7 | == | CAP2.2 + CAP1.1 + CAP3.3 | = | 6 + 3 + 8 |
| CT1-8 | == | CAP1.1 + CAP3.3 + CAP0.0 | = | 3 + 8 + 1 |
| CT1-9 | == | CAP3.3 + CAP0.0 + CAP2.0 | = | 8 + 1 + 2 |
| CT1-10 | == | CAP0.0 + CAP2.0 + CAP3.1 | = | 1 + 2 + 4 |
| CT1-11 | == | CAP2.0 + CAP3.1 + CAP1.3 | = | 2 + 4 + 12 |
| CT1-12 | == | CAP3.1 + CAP1.3 + CAP2.2 | = | 4 + 12 + 6 |
| CT1-13 | == | CAP1.3 + CAP2.2 + CAP0.2 | = | 12 + 6 + 5 |
| CT1-14 | == | CAP2.2 + CAP0.2 + CAP3.3 | = | 6 + 5 + 8 |
| CT1-15 | == | CAP0.2 + CAP3.3 + CAP1.3 | = | 5 + 8 + 12 |
| CT1-16 | == | CAP3.3 + CAP1.3 + CAP0.0 | = | 8 + 12 + 1 |

ENHANCING SENSITIVITY AND ROBUSTNESS OF MECHANICAL ROTATION AND POSITION DETECTION WITH CAPACITIVE SENSORS

REFERENCE TO RELATED APPLICATION

This application claims priority to, and the benefit of, U.S. Provisional Patent Application No. 62/453,575, entitled "Method of Enhancing Sensitivity and Robustness of Mechanical Rotation and Position Detection with Capacitive Sensors", and filed on Feb. 2, 2017, the entirety of which is hereby incorporated by reference.

BACKGROUND

User Interfaces (UIs) and human machine interfaces (HMIs) allow a user or operator to control a machine. Capacitive touch interfaces are becoming more popular, including capacitive touch displays that provide user input capabilities as well as display of data, graphics or other information to an operator. Capacitive position detection for HMI technology offers long life time, low implementation costs, and ease of use as a sealed fluid and gas proof control element, which is beneficial in areas of operation with explosives and chemical processes. Capacitive sensing can be used for detecting the position of a control actuator as well as for detecting user touch events. For example, capacitive position sensing for rotary and/or linear control elements of an HMI can be combined with user touch detection. Capacitive sensing systems may suffer from weak response of conductive structures or of a user's finger introduced into the sensitive area of an HMI control device.

SUMMARY

Described example user interface control apparatus includes a first structure, with a first side, conductive capacitor plate structures spaced along a first direction on the first side, a movable second structure with an auxiliary conductive structure, and an interface circuit to provide excitation signals to, and receive sense signals from, the conductive capacitor plate structures to perform a mutual capacitance test and a self-capacitance test of individual ones of the conductive capacitor plate structures to determine a position of the second structure or a user's finger relative to the first structure along the first direction.

DETAILED DESCRIPTION

Figure 1:
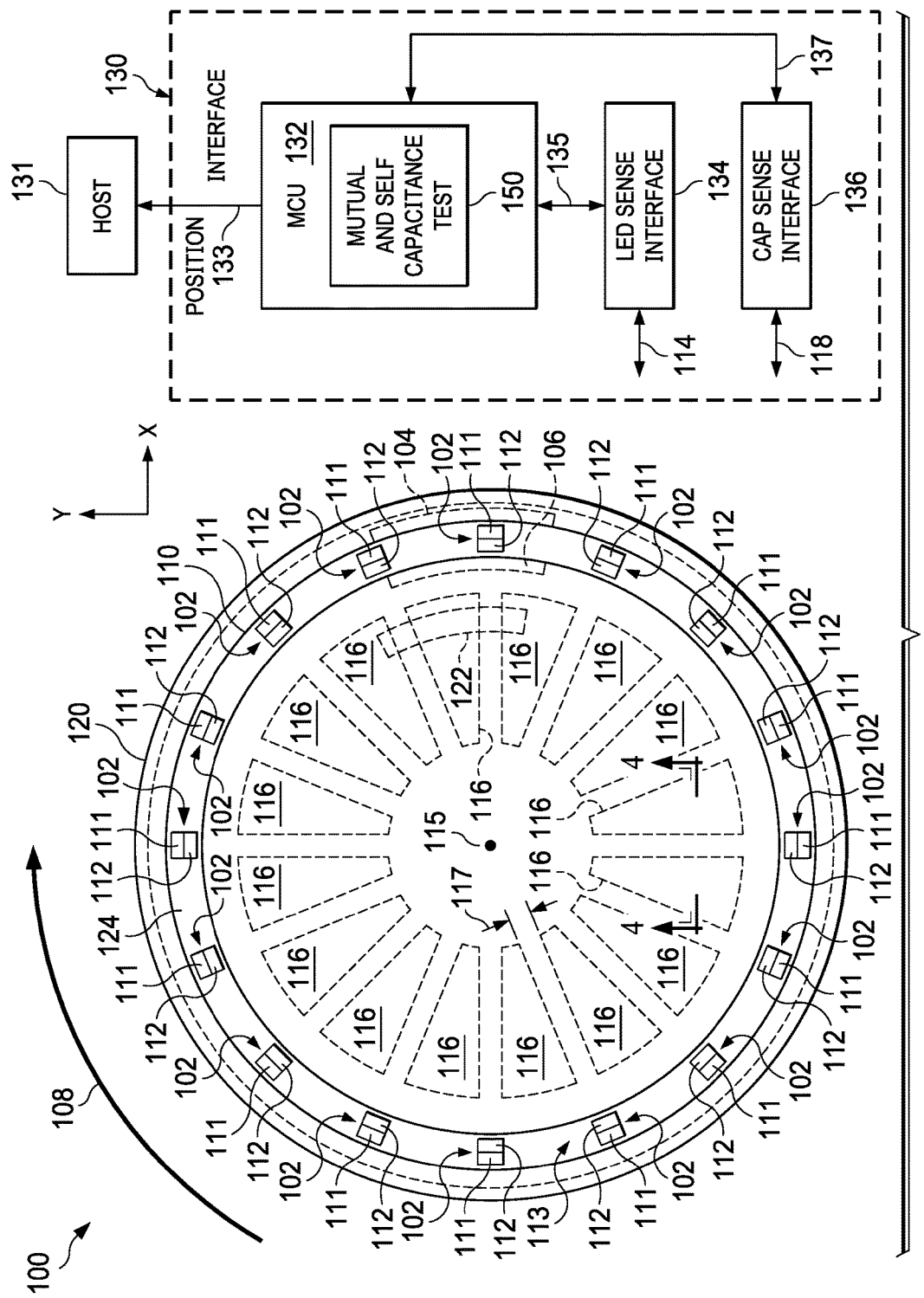
FIG. 1 is a top plan view of a rotational mechanical control apparatus including a stationary first structure and a rotatable second structure for a user interface with capacitive and optical rotational position and user touch detection.

In the drawings, like reference numerals refer to like apparatus throughout, and the various features are not necessarily drawn to scale. In the following discussion and in the claims, the terms "including", "includes", "having", "has", "with", or variants thereof are intended to be inclusive in a manner similar to the term "comprising", and thus should be interpreted to mean "including, but not limited to . . . " Also, the term "couple" or "couples" is intended to include indirect or direct electrical or mechanical connection or combinations thereof. For example, if a first device couples to or is coupled with a second device, that connection may be through a direct electrical connection, or through an indirect electrical connection via one or more intervening devices and connections.

FIG. 1 shows a rotational mechanical control apparatus 100 for a user interface. In one example, the apparatus 100 is a user interface control knob that can be mechanically rotated by a user. The control apparatus 100 can be used in any form of user interface or HMI, for example, industrial control panels, automobile dashboard controls, etc. The example of FIG. 1 provides a rotational control apparatus 100. Other possible examples include linear user interface control mechanisms, such as slider controls as illustrated and described below in connection with FIGS. 14 and 15. FIG. 1 is a top view of a control knob user interface control apparatus 100 which can be used for a variety of applications, such as a volume knob for a vehicle audio system, and can include a capacitive touch sense on/off button in certain implementations. The apparatus 100 includes conductive structures and pairs 102 of optical devices positioned on a fixed or stationary portion. A rotary portion includes reflector structures 104 and 106. The rotary structure is movable along a circumferential direction 108 relative to an axis 115 of the stationary portion. The optical device pairs 102 in one example are LEDs 111 and 112 positioned on the fixed or stationary portion, and one or more conductive structures positioned on a rotating structure. The control apparatus 100 includes electrical connections 114, such as PCB traces, to interface with the source and sensor optical devices 111 and 112.

The apparatus in this example includes capacitive sensing circuitry that detects the relative position of the rotating structure to the stationary structure by sensing capacitances associated with the conductive structures on the fixed portion. In this example, moreover, the top face of the rotating structure can be touched by a user's finger, and the capacitive sensing circuitry can detect user touch events as well as the position of the user's finger on the top face of the rotating structure. In certain examples, the apparatus 100 also includes optical position sensing features and associated circuitry to complement the capacitive position sensing functions. Described examples provide improved capacitive sensing structures alone or in combination with mutual and self-capacitance measurements with a conductive structure as field transducer to facilitate enhanced sensitivity for detecting user touch events and/or control apparatus position.

The example control apparatus 100 includes a stationary first structure 110 with a first (e.g., top or upper) side 113, facing out of the page in FIG. 1. The first structure 110 includes 16 conductive capacitor plate structures 116 spaced from one another along a circumferential first direction 108 on the first side 113. The conductive capacitor plate structures 116 are spaced from one another by a first distance 117 (labeled D1) along the first direction 108. The first structure 110 includes an integer number N=16 pairs 102 of LEDs 111, 112. In other examples, more or fewer than 16 conductive capacitor plate structures 116 and LED pairs 102 can be used. In one example, the individual LED pairs 102 include an optical source LED 111 and an optical sensor LED 112. The LEDs 111 in this example have a first wavelength, and the sensor LEDs 112 have a different wavelength. The control apparatus 100 includes electrical connections 118 to interface with the conductive capacitor plate structures 116.

The control apparatus 100 includes a second structure 120 that is movable relative to the first structure 110 along the first direction 108. The second structure 120 includes an auxiliary conductive structure 122 positioned on a second side 123 of the second structure 120 (e.g., bottom side, facing into the page in FIG. 1). The auxiliary conductive structure 122 moves with the second structure 120 along the first direction 108 to selectively modify a capacitance associated with a given one of the conductive capacitor plate structures 116 when the auxiliary conductive structure 122 is positioned proximate the given capacitor plate structure 116. The second structure 120 in this example also includes a transparent window or aperture 124 that allows light from the optical sources 111 to pass through the second structure 120.

The control apparatus 100 includes an interface circuit 130 that provides excitation signals to the conductive capacitor plate structures 116 and receives sense signals from the conductive capacitor plate structures 116 to measure capacitances of the apparatus 100. The interface circuit 130 performs a mutual capacitance test of groups of the conductive capacitor plate structures 116 and performs a self-capacitance test of individual ones of the conductive capacitor plate structures 116. The interface circuit 130 provides a position signal POSITION to a host system 131. The position signal represents a position of the second structure 120 or a user's finger relative to a position of the first structure 110 along the first direction 108 according to signals from the conductive capacitor plate structures 116 during one or both of the mutual capacitance test and the self-capacitance test. In one example, the interface circuit 130 also determines the position signal POSITION at least partially according to signals from the optical sensors 112, in addition to the signals from the capacitor plate structures 116.

In one example, the interface circuit 130 is provided on the PCB of the first user interface structure 110. The interface circuit 130 in FIG. 1 includes a processor, such as a microcontroller unit (MCU) 132 with a communications interface or output 133 that provides the position signals POSITION to the host circuit 131. The host circuit 131 in one example is a processor or user interface controller to operate a system according to one or more control elements including the rotary knob control apparatus 100. The processor 132 can be any suitable digital logic circuit, programmable or pre-programmed, such as an ASIC, microprocessor, microcontroller, DSP, FPGA, etc., that operates to execute program instructions stored in an internal or external electronic memory (not shown) to implement the features and functions described herein as well as other associated tasks to implement a user interface control apparatus 100. In certain examples, the memory constitutes a non-transitory computer-readable storage medium that stores computer-executable instructions that, when executed by the processor 132, perform the various features and functions detailed herein.

The illustrated interface circuit 130 also includes an optical (e.g., LED) sense interface circuit 134 and a capacitive sense interface circuit 136. The processor 132 exchanges data and signaling with the LED sense interface circuit 134 via a communications interface connection 135. The sense interface circuit 134 is connected to the electrical connections 114 to interface with the source and sensor optical devices 111 and 112. The capacitive sense interface circuit 136 is connected to the electrical connections 118 to interface with the conductive capacitor plate structures 116. The processor 132 exchanges data and signaling with the capacitive sense interface circuit 136 via a communications interface connection 137. The processor 132 in one example executes program instructions to implement a mutual and self-capacitance test function or component 150.

Figure 2:
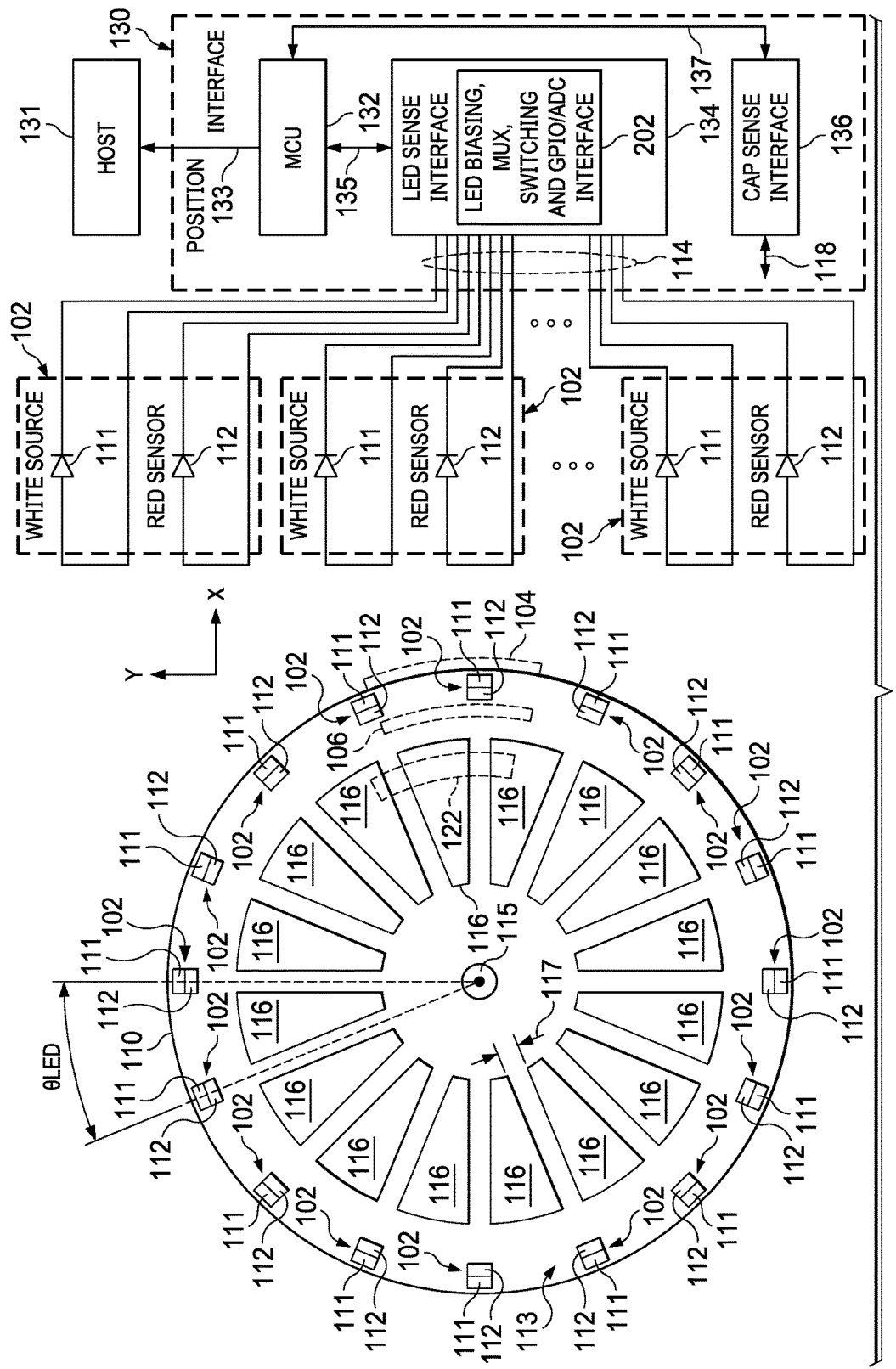
FIG. 2 is a top plan view of the stationary first structure of the control apparatus of FIG. 1 with schematically illustrated optical rotational position detection circuitry.

FIG. 2 shows a top view of the stationary first structure 110 with the second structure 120 removed. The reflector structures 104, 106 and the auxiliary conductive structure 122 of the second structure 120 are shown in dashed line form for reference in FIG. 2. FIG. 2 schematically illustrates an example of the interconnection of the LEDs 111 and 112 with the LED sense interface circuit 134. The interface circuit 134 includes circuitry 202 for optical device biasing, signal multiplexing and switching, and general purpose input/output (GPIO) interfacing between the processor 132 and the LEDs 111, 112. In one example, the circuit 134 includes biasing LED circuitry 202 to selectively forward or reverse bias selected ones of the LEDs 111 and/or 112. For example, the circuit 134 forward biases one, some or all of the source LEDs 111 and reverse biases the sensor LEDs 112. The forward biasing causes the selected source LED(s) 111 to emit or transmit light of an associated first wavelength λ1. Reverse biasing allows the selected sensor LED(s) 112 to sense light of an associated second wavelength λ2 or less.

The wavelengths λ1 and λ2 can be the same or different. In the illustrated examples, the first wavelength λ1 is less than or equal to the second wavelength λ2. In one example, the source LEDs 111 are white LEDs and the sensor LEDs 112 are red LEDs. The electrical connections 114 allow the circuit 202 to selectively control the anode and cathode voltages and signal conditions of each of the LEDs 111 and 112. The processor 132 in certain implementations includes one or more analog to digital converters (ADCs or A/Ds, not shown), and the circuit 202 includes switching circuitry and voltage supply and signal generators to selectively provide forward and reverse biasing of individual source LEDs 111 and interconnection of selected sensor LEDs 112 to GPIO terminals configured as ADC inputs. This allows the processor 132 to obtain digital values representing the sensor LED voltages to determine whether a given sensor LED 112 is receiving a threshold amount of light from the associated source LED 111 when the source LED 111 is forward biased. This, in turn, allows the processor 132 to determine whether each given optical device pair 102 is proximate to the movable reflector structure(s) 104, 106, and hence to determine the position of the second structure 120 within the angular spacing resolution θLED of the optical device pairs 102 (e.g., 22.5 degrees in the illustrated example).

In other examples, the LED interface circuitry 202 includes multiplexers (not shown) to allow sharing of a limited number of ADC inputs, and the optical device pairs 102 can be actuated and measured individually or in groups. The circuit 134 can include ADC circuits (with or without input multiplexing), and the ADC circuits provide converted values to the processor 132. In some examples, the processor 132 includes GPIO terminals that can be dynamically configured as digital outputs, digital inputs, analog outputs, analog inputs and/or ADC inputs. In certain examples, the circuit 202 selectively connects individual LED terminals to a high voltage level, a low voltage level, and a DC input or provides a high impedance. The processor 132, in certain examples, controls the LED sense interface circuit 134 in multiphase operations to selectively forward bias one or more of the source LEDs 111 and to reverse bias selected ones of the sensor LEDs 112 to obtain sensor readings and determine the rotational position of the reflector structure or structures 104, 106 relative to the first structure 110.

Figure 3:
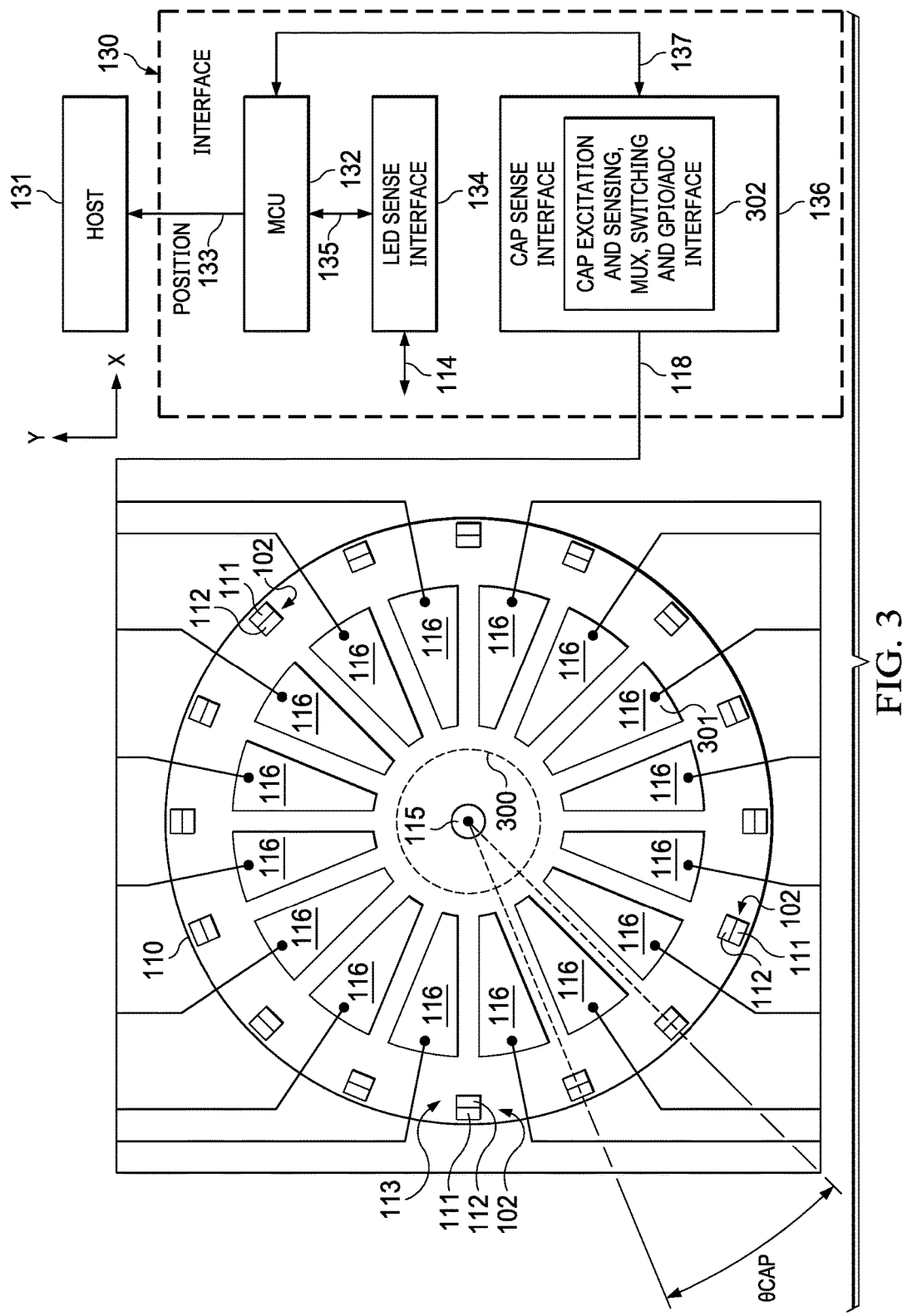
FIG. 3 is a top plan view of the stationary first structure of the control apparatus of FIG. 1 with schematically illustrated capacitive rotational position and user touch detection and interface circuitry.

FIG. 3 shows a top view of the first structure 110 and schematically illustrates the capacitive rotational position and user touch event detection sense interface circuit 136. As seen in FIGS. 4-8 below, the first structure 110 in one example includes a transparent overlay formed above the top side 113 of the first structure 110, not shown in FIG. 3. The circuit 136 includes capacitor excitation and sensing circuitry 302 that selectively provides excitation voltage or current signals to the capacitor plate structures 116 via the interconnections 118. The circuit 302 also allows connection of ADC inputs (e.g., of internal ADC circuits or GPIO/ADC inputs of the processor 132) to one or more of the plate structures 116 to sense capacitor voltage and/or current signals to determine capacitance changes. The circuit 302 also allows connection of one or more of the plate structures 116 to a controlled voltage to set the voltage values of individual structures 116. The circuit 302 also allows floating of one or more of the plate structures 116, for example, by providing a high impedance (e.g., HI-Z) connection to selected ones of the structures 116.

The circuitry 136 in one example provides signals or converted values representing voltage and/or currents of the capacitors formed by the plate structures 116 from which the processor 132 can detect threshold amounts of capacitance variations caused by proximity of the conductive structure 122 of the second structure 120 (FIG. 1) and/or a user's finger to a given one or group of the plate structures 116. From this, the processor 132 can determine the rotational position of the conductive structure 122 and/or the user's finger on the tope surface of the second structure 120, relative to the stationary first structure 110.

In other examples, the auxiliary conductive structure 122 extends at least partially over or near one or more conductive PCB traces or other copper area connected in fixed manner to a reference voltage (e.g., GND) or to a GPIO, which can switch that copper to GND or supply level or other voltage level, or to a high impedance state, to enhance the response generated by the conductive structure 122. Example designs facilitate distinguishing the presence of the structure 122 from the response of a user's finger touching the top surface of the structure 120 in the wheel electrode area, as this touch event and respective capacitive response would not be influenced by this GND-VCC-input switching.

In the example control apparatus 100 of FIGS. 1-3, the interface circuit 130 performs a series of mutual capacitance tests of individual groups of the conductive capacitor plate structures 116 and one or more self-capacitance tests of individual given ones of the conductive capacitor plate structures 116. For these tests, the interface circuit 130 provides an excitation signal to the given conductive capacitor plate structure 116 and receives a sense signal from that structure 116 or from a neighboring conductive capacitor plate structure 116. The interface circuit 130 processes the received signals and determines (e.g., computes) mutual and self-capacitances (e.g., values that represent a measured capacitance) according to (e.g., in response to or based upon) the corresponding sense signal. The interface circuit 130 processes the measured capacitances to identify the relative position of the first user interface structure 110 and the user's finger and/or the relative position of the first user interface structure 110 and the second user interface structure 120 according to the mutual capacitances and one or more self-capacitances associated with the individual conductive capacitor plate structures 116.

Figure 4:
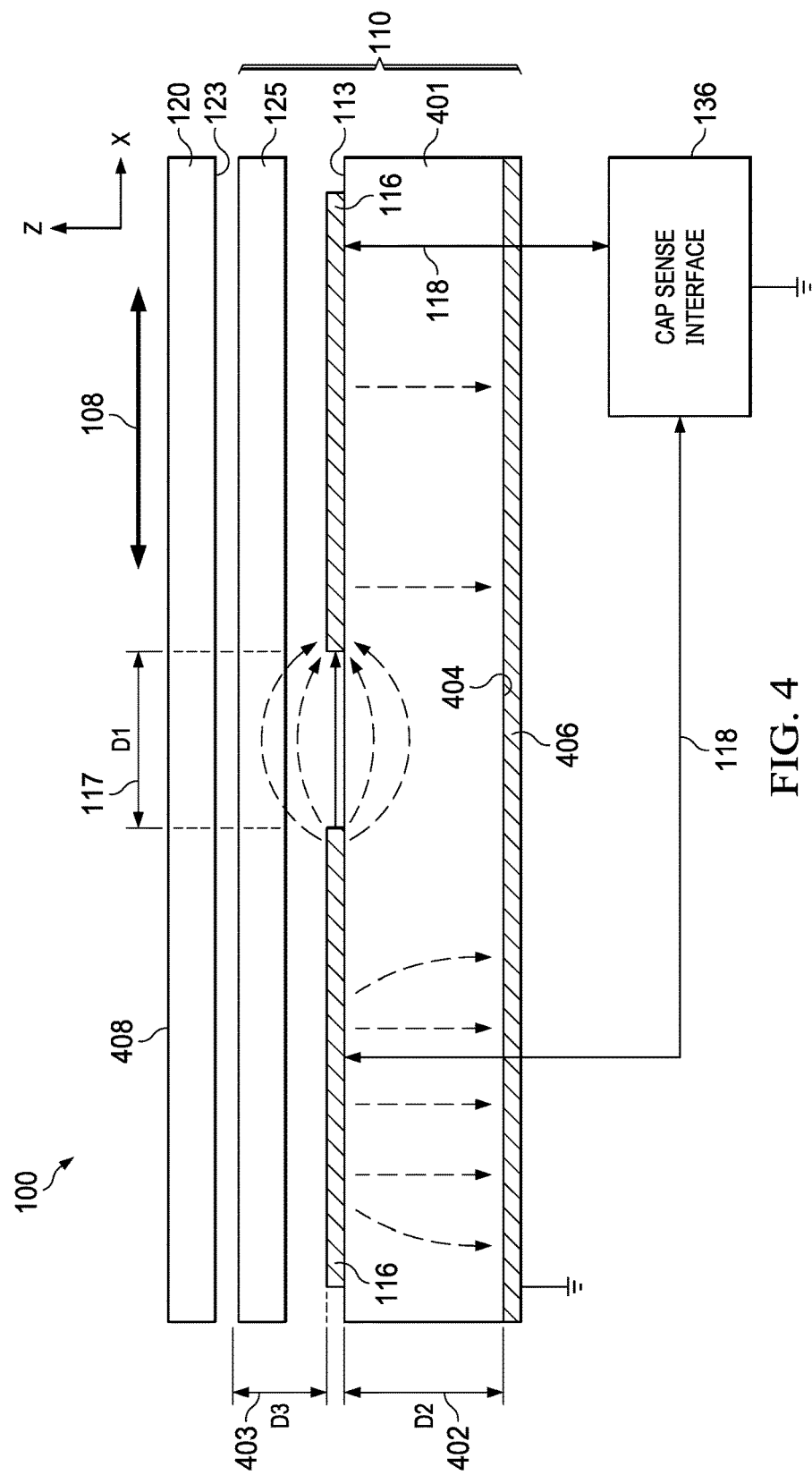
FIGS. 4-8 are a partial sectional side elevation view taken along line 4-4 of the control apparatus of FIG. 1 showing example electric field lines during mutual capacitance and self-capacitance measurement for position and/or user touch detection.
Figure 5:
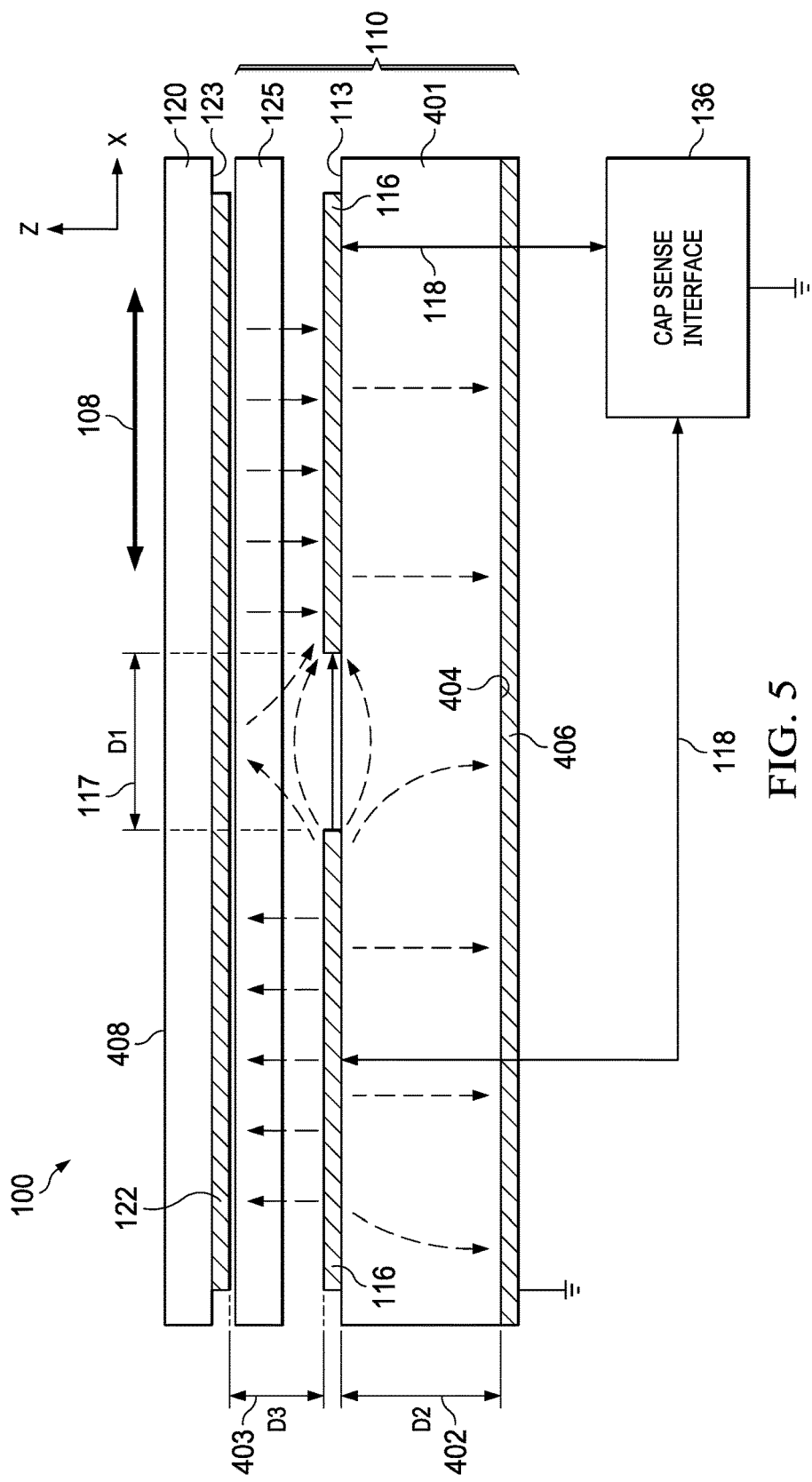
Figure 6:
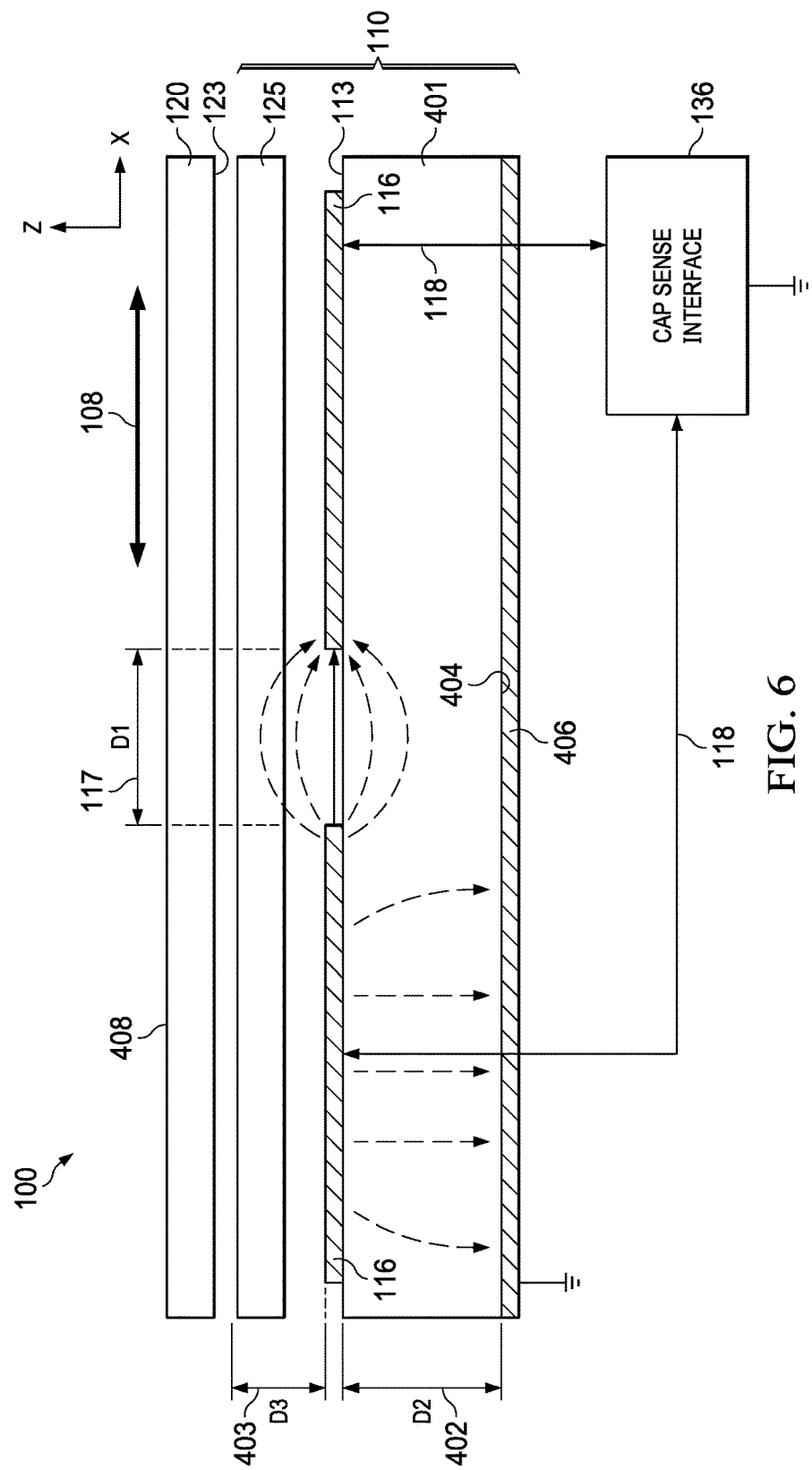
Figure 7:
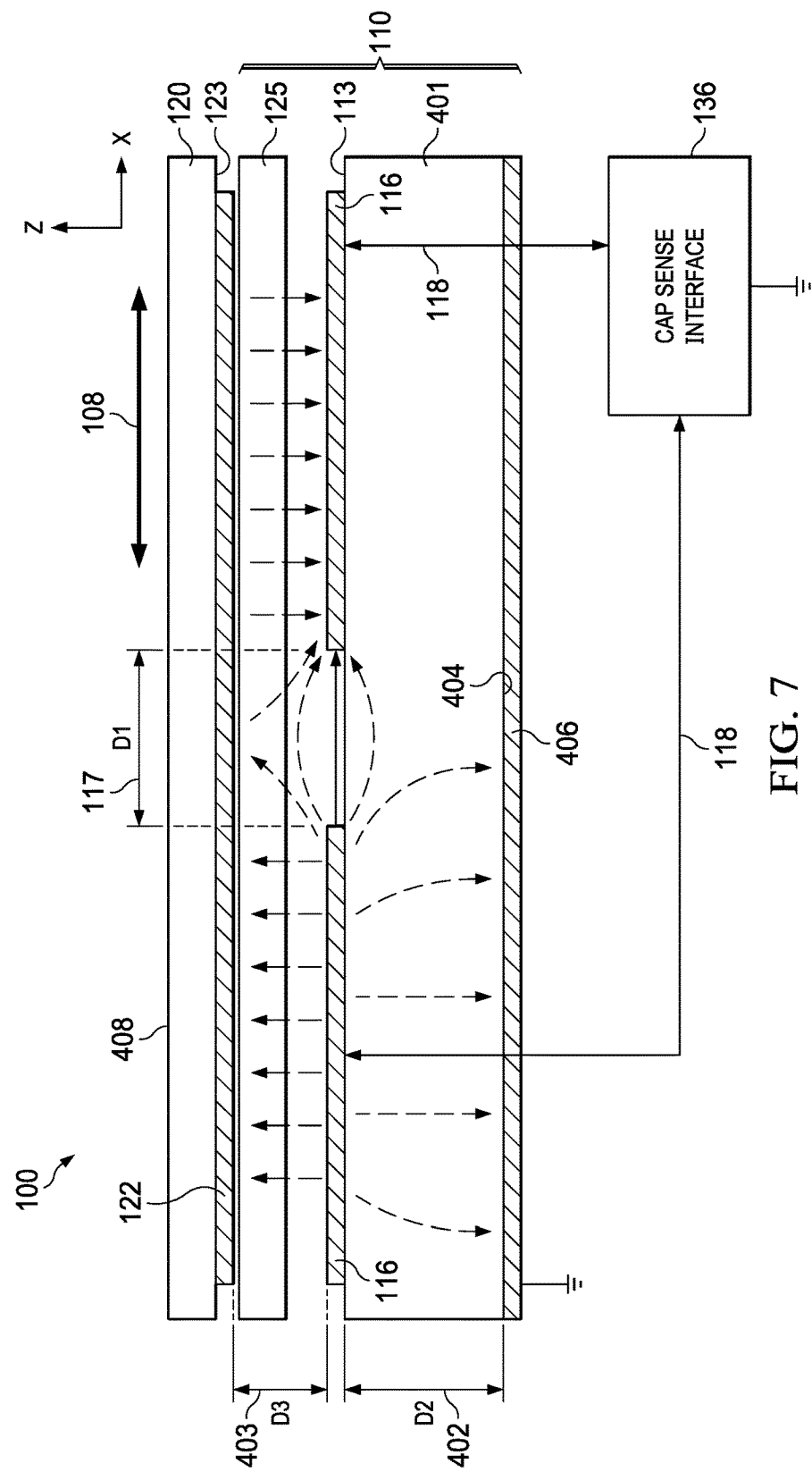
Figure 8:
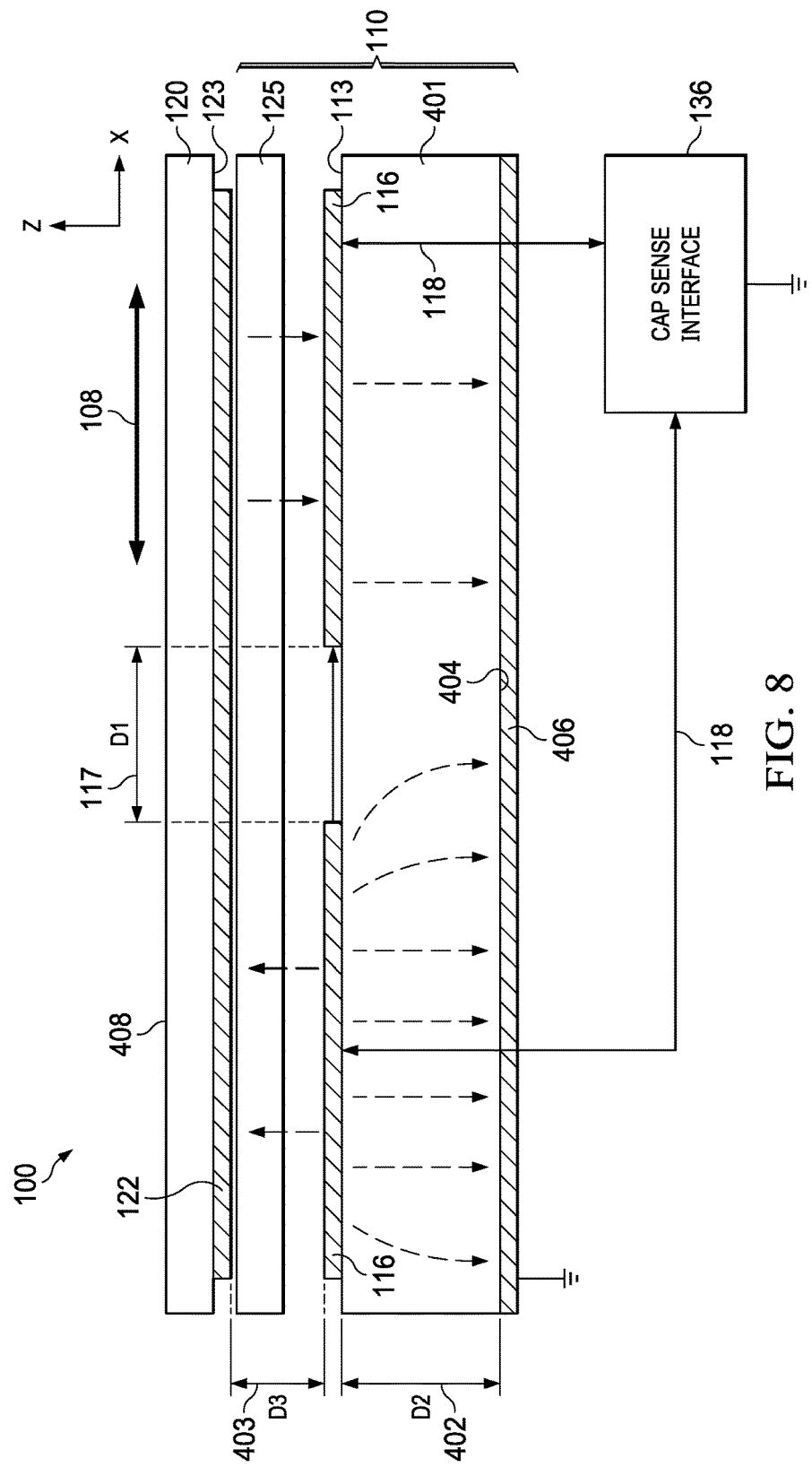
Figure 9:
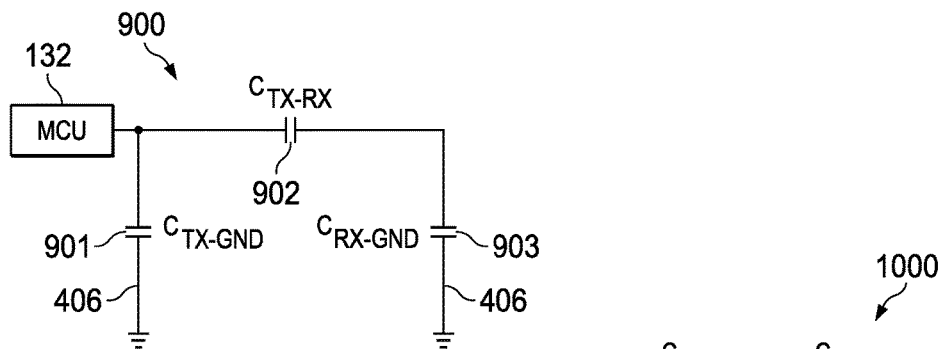
FIG. 9 is a schematic diagram of a mutual capacitance measurement circuit configuration example in the apparatus of FIG. 4 with no proximate auxiliary conductive structure present.
Figure 10:
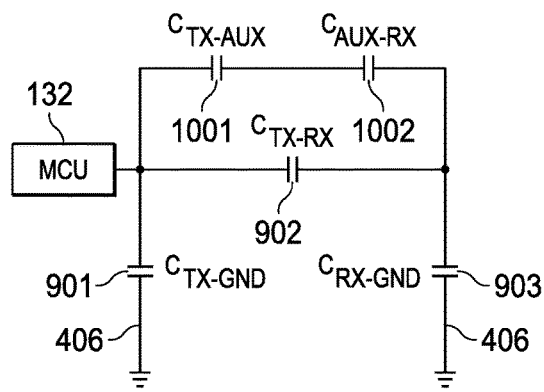
FIG. 10 is a schematic diagram of a mutual capacitance measurement circuit configuration example in the apparatus of FIG. 5 in the presence of an auxiliary conductive structure.

Referring also to FIGS. 4-10, FIGS. 4 and 5 show partial sectional side elevation views taken along line 4-4 in FIG. 1 to illustrate example electric field lines during mutual capacitance measurements or tests in the control apparatus 100. FIGS. 6-8 show partial sectional side elevation views taken along line 4-4 in FIG. 1 to illustrate example electric field lines during self-capacitance measurement for position and/or user touch detection in the control apparatus 100 FIGS. 6 and 7 show testing with a neighboring electrode grounded, and FIG. 8 shows testing with the neighboring electrode floating (e.g., HIZ or high impedance state). FIG. 9 shows a mutual capacitance measurement circuit configuration example in the apparatus of FIG. 4 with no proximate auxiliary conductive structure 122 present. FIG. 10 shows the mutual capacitance measurement circuit configuration example in the apparatus of FIG. 5 in the presence of the auxiliary conductive structure 122.

The conductive capacitor plate structures 116 are spaced from one another by a first distance 117 (labeled D1 in the drawings) along the first direction 108 (e.g., in the X direction for the illustrated portion of the apparatus 100 in FIGS. 4-8. The first structure 110 includes a printed circuit board (PCB) 401 that includes the first side 113 with the conductive capacitor plate structures 116, and a second side 404 opposite to the first side 113. In addition, the first structure 110 includes a transparent overlay structure 125. The PCB 401 includes a further conductive structure 406 (e.g., a ground plane) on the second side 404. The further conductive structure 406 is spaced from the conductive capacitor plate structures 116 by a second distance 402 (labeled D2) along a second direction (e.g., the Z direction in FIGS. 4-8). As shown in FIG. 5, the auxiliary conductive structure 122 is spaced from the conductive capacitor plate structures 116 by a third distance 403 (labeled D3) along the second direction. In this example, the first and second directions are perpendicular to one another, although not a requirement of all possible implementations. In the illustrated examples, the second distance 402 D2 is greater than the first distance 117 D1, and the first distance 117 D1 is greater than the third distance 403 D3. This configuration enhances the sensitivity of the system to the relative positioning of the auxiliary conductive structure 122 and the conductive capacitor plate structures 116. The relative dimensions D1, D2 and D3 also improve the sensitivity for detecting touch events by a user's finger (not shown) touching a top surface 408 of the second structure 120. The distance D3 in one implementation is made as short as possible, and the gap distance D1 between neighboring structures 116 is made at least equal the distance D2 to GND, unless a driven shield (not shown) is provided between the TX/RX electrodes 116 and GND.

In certain implementations, the processor 132 performs a mutual capacitance measurement as well as a single self-capacitance measurement with respect to each given conductive capacitor plate structure 116. In other implementations, the processor 132 performs a mutual capacitance measurement in addition to multiple self-capacitance measurements with respect to each conductive capacitor plate structure 116. The processor 132 in one example performs the measurement sequence periodically in order to continuously monitor the control apparatus 100 with respect to the position of the second structure 120 relative to the first structure 110, in addition to monitoring for detected user touch events. In each sequence, in one example, the processor 132 implements multiple mutual capacitance measurements (e.g., with respect to each of the example 16 given structures 116), and two sets of multiple self-capacitance measurements (e.g., with respect to each of the example 16 given structures 116), and obtains multiple sets of measured capacitances. In the illustrated example, the processor 132 compares the measured capacitance values of each measurement set, and determines the position of the rotatable second structure 120 based on the maximal (e.g., highest) measured capacitances and the corresponding locations of the maximal measurements. In addition, the processor 132 in one example distinguishes between identified second structure position and user touch events based on the measured capacitance values.

FIGS. 4, 5, 9 and 10 illustrate example mutual capacitance testing with respect to a given conductive capacitor plate structure 116. During the mutual capacitance testing, the interface circuit 130 provides an excitation signal to the given conductive capacitor plate structure 116 (e.g., the transmit or TX electrode) and receives a sense signal from one or more neighboring conductive capacitor plate structures 116 (e.g., the receive or RX electrode). FIGS. 4 and 5 show this test configuration and corresponding field lines (arrows in the drawings) for testing the mutual capacitance of a given structure 116 on the left, and a neighboring structure 116 on the right. It will be appreciated that the given structure 116 can have a similarly connected neighbor to the left (not shown in FIGS. 4-8). FIG. 4 shows the situation in which the rotatable auxiliary conductive structure 122 is not near the given or neighboring structures 116. FIG. 5 shows the situation in which the rotatable auxiliary conductive structure 122 at least partially overlies the given conductive capacitor plate structure 116 and the neighboring structure 116.

FIG. 9 shows a schematic circuit representation 900 of the situation in FIG. 4 when the auxiliary conductive structure 122 is not proximate the given and neighboring electrode structures 116. The diagram 900 in FIG. 9 illustrates a first capacitance 901 (labeled $C_{TX-GND}$) that represents the capacitance between the given (e.g., TX) conductive capacitor plate structure 116 and the ground plane conductive structure 406. The diagram 900 also shows a second capacitance 902 (labeled $C_{TX-RX}$) that represents the capacitance between the given and neighboring structures 116, as well as a third capacitance 903 (labeled $C_{RX-GND}$) that represents the capacitance between the neighboring (e.g., RX) conductive capacitor plate structure 116 and the ground plane structure 406. In this case the auxiliary structure 122 is not present, thus the electric field $E_{TX-RX}$, which is primarily responsible for the sensed signal at the RX electrode, is mainly defined by the gap between TX and RX electrodes 116.

FIG. 10 shows a schematic circuit representation 1000 of the situation in FIG. 5 in the presence of the auxiliary conductive structure 122. In this case, the capacitances 901, 902 and 903 are present in the circuit. In addition, the circuit includes a capacitance 1001 (labeled $C_{TX-AUX}$) that represents the capacitance between the given (e.g., TX) conductive capacitor plate structure 116 and the proximate auxiliary conductive structure 122, as well as a capacitance 1002 (labeled $C_{AUX-RX}$) that represents the capacitance between the auxiliary conductive structure 122 and the neighboring (e.g., RX) conductive capacitor plate structure 116. In this case the auxiliary conductive structure 122 is present, which reduces the electric field $E_{TX-RX}$, but adds an ETX-RX component that includes of the serial E-fields $E_{TX-AUX}$ $E_{AUX-RX}$ which are now all together responsible for the sensed signal at the RX electrode 116. Due to the larger capacitance $C_{TX-RX}$, the sensed signal at the RX electrode 116 will be significantly higher than in FIGS. 4 and 9, and the processor 132 can detect the presence of the auxiliary conductive structure 122.

The electrode configuration of TX and RX electrodes is controlled by program instructions executed by the processor 132, and the configuration of the electrodes can be changed from TX to RX and vice versa. In addition, the electrodes 116 are not only a combination of TX/RX pairs, but the TX/RX can commute around the wheel structure, and the TX electrode at the same time can be TX for two neighbored electrodes 116, configured as RX electrodes, one in the clockwise, and the other in the counter clockwise direction. In this manner, the processor 132 performs a differential measurement in certain examples, as the auxiliary structure 122 can be designed to cover the area of two neighbored electrodes 116.

In one example, the MCU processor 132 implements the mutual and self-capacitance test component 150 and the capacitor sensor interface circuit 136 connects the given structure 116 (e.g., TX) to an analog output general-purpose I/O (GPIO) of the processor 132 in order to provide a transmit (TX) signal to the given conductive capacitor plate structure 116. The processor 132 and the interface circuit 136 connects the neighboring structure 116 (e.g., the RX electrode) to an analog to digital converter (ADC) function of a different GPIO of the processor 132 in order to measure a received signal from the neighboring conductive capacitor plate structure 116. Any suitable AC, DC or ramping excitation (e.g., TX) signal can be applied to the given conductive capacitor plate structure 116 operating as a TX electrode. In one example, the processor 132 applies a series of excitation signals to the TX electrode 116 by operating a connected GPIO that acts as an analog output signal source. In one example, the excitation signal patterns include a first signal that ramps up from a ground level or other predefined level to charge the capacitances to a constant predetermined DC level.

Once the capacitances are set to a known starting state, the processor 132 switches the TX GPIO to a function that supports transfer of the existing charge to apply or create charge on the RX electrode 116 by the TX-RX capacitance. After one charge cycle, the processor switches to a transfer mode that transfers the created charge of the RX electrode 116 to an internal reference or sample capacitor of the MCU 132 or of the measuring (e.g., RX) GPIO, or to a reference capacitance of the capacitor sensor interface circuitry 136. In one example, a charge transfer circuit transfers the created RX electrode charge to the reference capacitor. The processor measures the number of internal clock cycles to charge the internal capacitance to a known value. Because the internal capacitance value is known, the processor 132 determines the measured capacitance (e.g., mutual or self-capacitance) according to (e.g., in response to or based upon) the number of required charge cycles to reach a certain threshold voltage on the reference capacitance. In this example, the processor 132 effectively measures the charge transfer to determine the measured capacitance. In other examples, the processor 132 uses a fixed charge time and measures the resulting electrode voltage to determine the measured capacitance. In other examples, the processor 132 uses a single charge or discharge slope to perform capacitance measurement. In one example, the processor 132 uses a voltage threshold and measures the time. In some examples, the processor 132 implements multiple charge and discharge cycles (e.g., oscillations) during a fixed gate time, and measures the number of charge discharge/oscillation cycles to determine the capacitance. In these examples, the processor 132 provides the excitation signal to the given conductive capacitor plate structure 116 and receives the sense signal from a neighboring conductive capacitor plate structure 116 to perform the mutual capacitance test of the individual groups of the conductive capacitor plate structures 116. In certain examples, moreover, the processor 132 uses two adjacent neighboring conductive capacitor plate structures 116 in performing capacitance testing of a given conductive capacitor plate structure 116 for the mutual capacitance measurements.

FIGS. 6 and 7 illustrate a first one of two different example self-capacitance measurements in the control apparatus 100. FIG. 6 shows a first self-capacitance measurement configuration and associated field lines with the given conductive capacitor plate structure 116 connected to receive an excitation signal from a corresponding GPIO of the processor 132. The given structure 116 operates as both a TX electrode and an RX electrode for the self-capacitance measurements. In the example of FIG. 6, the processor 132 grounds the neighboring structure 116 (e.g., the same potential as the ground plane structure 406) using a connected GPIO. FIG. 7 shows the first self-capacitance measurement configuration and corresponding electric field lines in the presence of the auxiliary conductive structure 122, which changes the field lines and the corresponding measured self-capacitance associated with the given conductive capacitor plate structure 116. In one example, the processor 132 performs the first self-capacitance test for the individual conductive capacitor plate structures 116 by providing the excitation signal to the given conductive capacitor plate structure 116, setting the voltage of the neighboring conductive capacitor plate structure 116 to a first voltage value (e.g., ground as in FIGS. 6 and 7) while providing the excitation signal to the given conductive capacitor plate structure 116. The processor 132 receives the sense signal from the given conductive capacitor plate structure 116, and determines a first self-capacitance associated with the given conductive capacitor plate structure 116 according to the corresponding sense signal.

FIG. 8 shows a second self-capacitance measurement in the control apparatus 100. In this example, the processor 132 performs the second self-capacitance test for the individual conductive capacitor plate structures 116 by providing the excitation signal to the given conductive capacitor plate structure 116 and setting the voltage of the neighboring conductive capacitor plate structure 116 to a second voltage value or allowing the neighboring conductive capacitor plate structure 116 to float while providing the excitation signal to the given conductive capacitor plate structure 116. The processor 132 receives the sense signal from the given conductive capacitor plate structure 116, and determines a second self-capacitance associated with the given conductive capacitor plate structure 116 according to the corresponding sense signal. In this example, the processor 132 processes the measured capacitances to identify the relative position of the first user interface structure 110 and the user's finger or the second user interface structure 120 according to the mutual capacitances and first and second self-capacitances associated with the individual conductive capacitor plate structures 116.

The processor 132 in one example can distinctly identify the presence or absence of the auxiliary conductive structure 122 and/or the presence or absence of a user's finger at a given location along the direction 140 based on measured capacitance values obtained in each measurement cycle according to (e.g., in response to or based upon). In one example, the processor 132 performs a mutual capacitance measurement as well as first and second self-capacitance measurements for each of the 16 given electrodes (e.g., capacitor plate structures) 116 in each measurement cycle, and computes 16 sets of three capacitance measurements.

In another example, the processor 132 performs the capacitance measurements with respect to the first and second neighboring electrodes for each given electrode 116, and computes 16 sets of five capacitance measurements (e.g., a mutual capacitance measurement, a first self-capacitance measurement relative to the first neighboring electrode, a first self-capacitance measurement relative to the second neighboring electrode, a second self-capacitance measurement relative to the second neighboring electrode, and a second self-capacitance measurement relative to the second neighboring electrode). In one example, the processor 132 differentiates according to the difference between the first and second measured self-capacitance values for the individual given electrodes 116, referred to hereinafter as a self-capacitance difference value. In the described examples illustrated in FIGS. 4-8, the self-capacitance difference value is greatest with respect to a given electrode 116 for the case where the auxiliary conductive structure 122 and a user's finger are proximate the given electrode 116. This condition corresponds to the highest electric field strength associated with the corresponding neighboring electrode 116. A lower self-capacitance difference value corresponds to the case where the auxiliary conductive structure 122 is present, and no user finger is present at or near the given electrode 116. A still lower self-capacitance difference value occurs when the user's finger is present, and the auxiliary conductive structure 122 is absent, and the lowest self-capacitance difference value corresponds to the case where no user's finger is present and the auxiliary conductive structure 122 is absent. The processor 132 in one example compares the measured capacitance values to determine the relative levels for the first and second self-capacitance values to distinguish these four conditions, and selectively identifies the position of the movable auxiliary conductive structure 122 and/or the presence and position of a user's finger in the control apparatus 100. In addition, the processor 132 in certain examples differentiates between potential positioned identifications based on the presence of multiple auxiliary conductive structures 116, for example, as shown in FIGS. 11-13.

Figure 11:
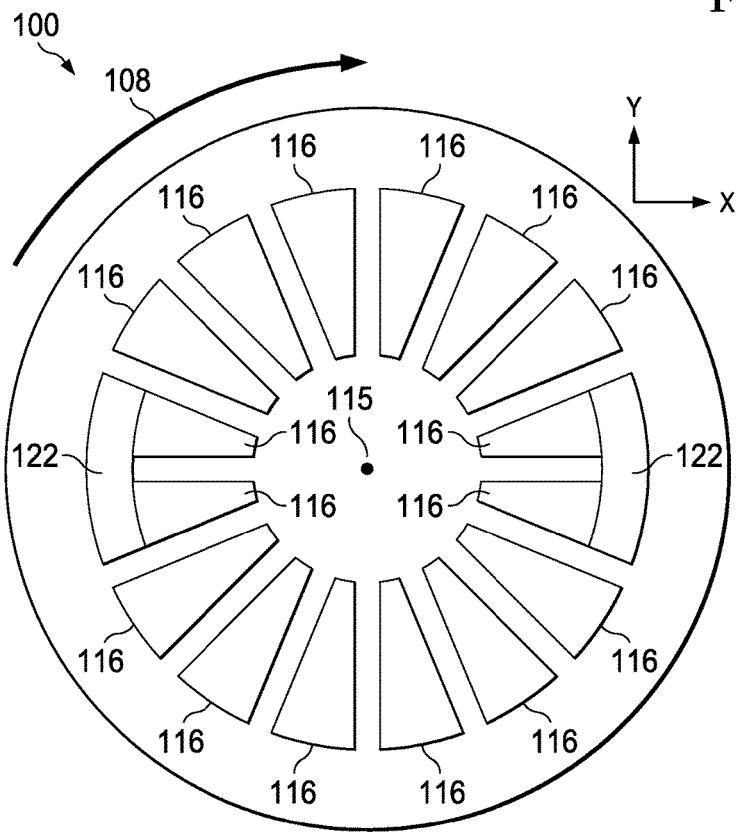
FIG. 11 is a partial top plan view of conductive capacitor plate structures and two example movable auxiliary conductive structures with angular circumferential lengths approximately covering radially outer portions of two neighboring capacitor plate structures.
Figure 13:
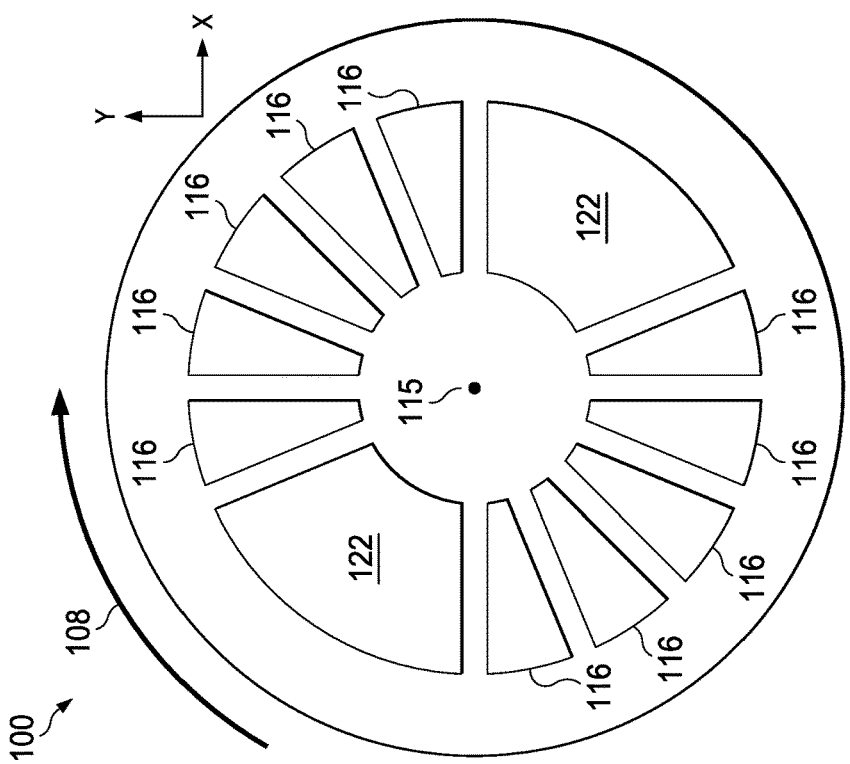
FIG. 13 is a partial top plan view of conductive capacitor plate structures and two example movable auxiliary conductive structures approximately covering the circumferential and radial extent of three neighboring capacitor plate structures.
Figure 12:
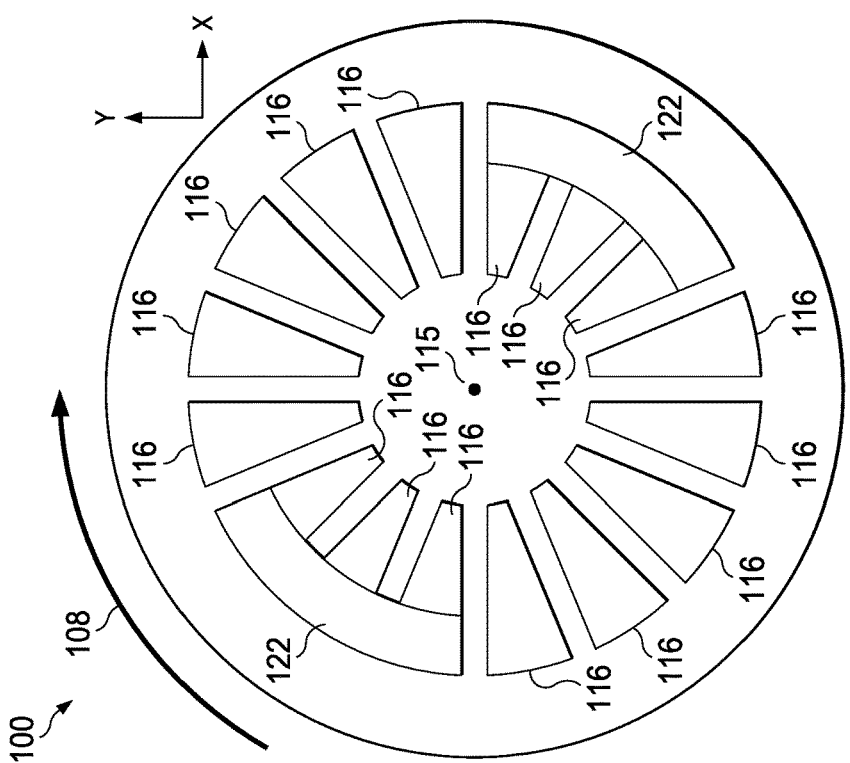
FIG. 12 is a partial top plan view of conductive capacitor plate structures and two example movable auxiliary conductive structures with angular circumferential lengths approximately covering radially outer portions of three neighboring capacitor plate structures.

FIGS. 11-13 illustrate different example conductive capacitor plate structure shapes and auxiliary conductive structure shapes which can be used. In addition, different numbers of auxiliary and capacitive structures can be used in different implementations. FIG. 11 shows an example including two movable auxiliary conductive structures 122 with angular circumferential lengths approximately covering radially outer portions of two neighboring capacitor plate structures 116 The auxiliary conductive structures 122 in this example are positioned on radially opposite sides of the axis 115, although not a strict requirement of all possible implementations. FIG. 12 shows another non-limiting example of the 16 conductive capacitor plate structures 116 and two example movable auxiliary conductive structures 122. In this example, the auxiliary structures 122 have angular circumferential lengths approximately covering radially outer portions of three neighboring capacitor plate structures 116. FIG. 13 shows yet another example with 16 conductive capacitor plate structures 116 and two example movable auxiliary conductive structures 122 that approximately cover the circumferential and radial extent of three neighboring capacitor plate structures 116. The radial extent of the auxiliary conductive structures 122 in one example covers a significant radial spacing of the conductive capacitor plate structures 116, and can even cover them radially completely as shown in FIG. 13. A larger covered area results in a higher robustness of the capacitive-mechanical rotation detection due to a higher response.

Figure 14:
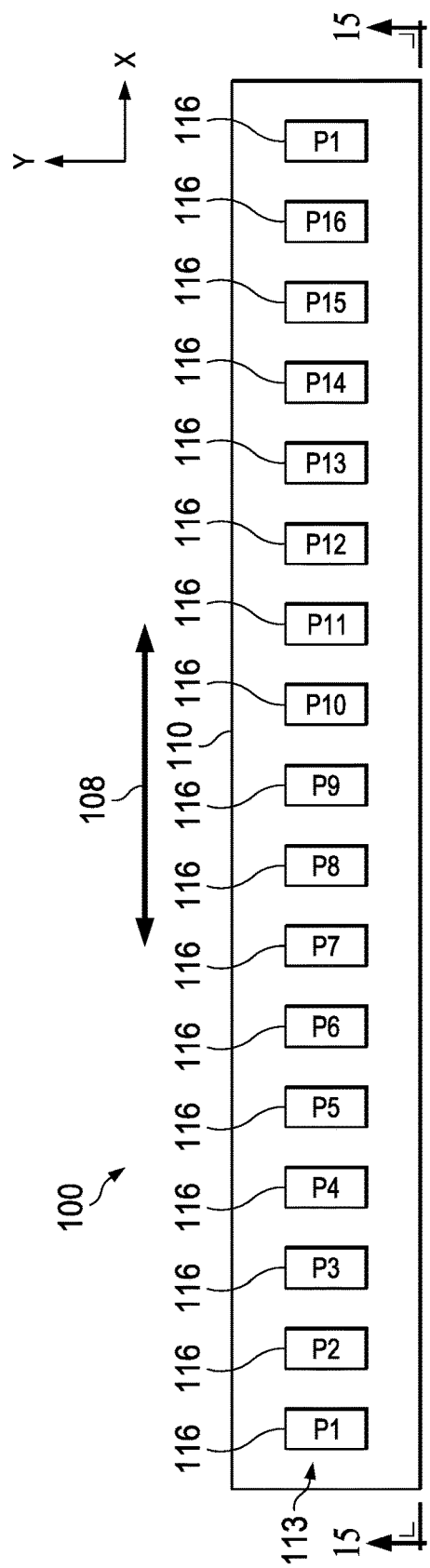
FIG. 14 is a top plan view of a linear mechanical control apparatus including a stationary first structure and a translatable second structure for a user interface with capacitive position and user touch detection.
Figure 15:
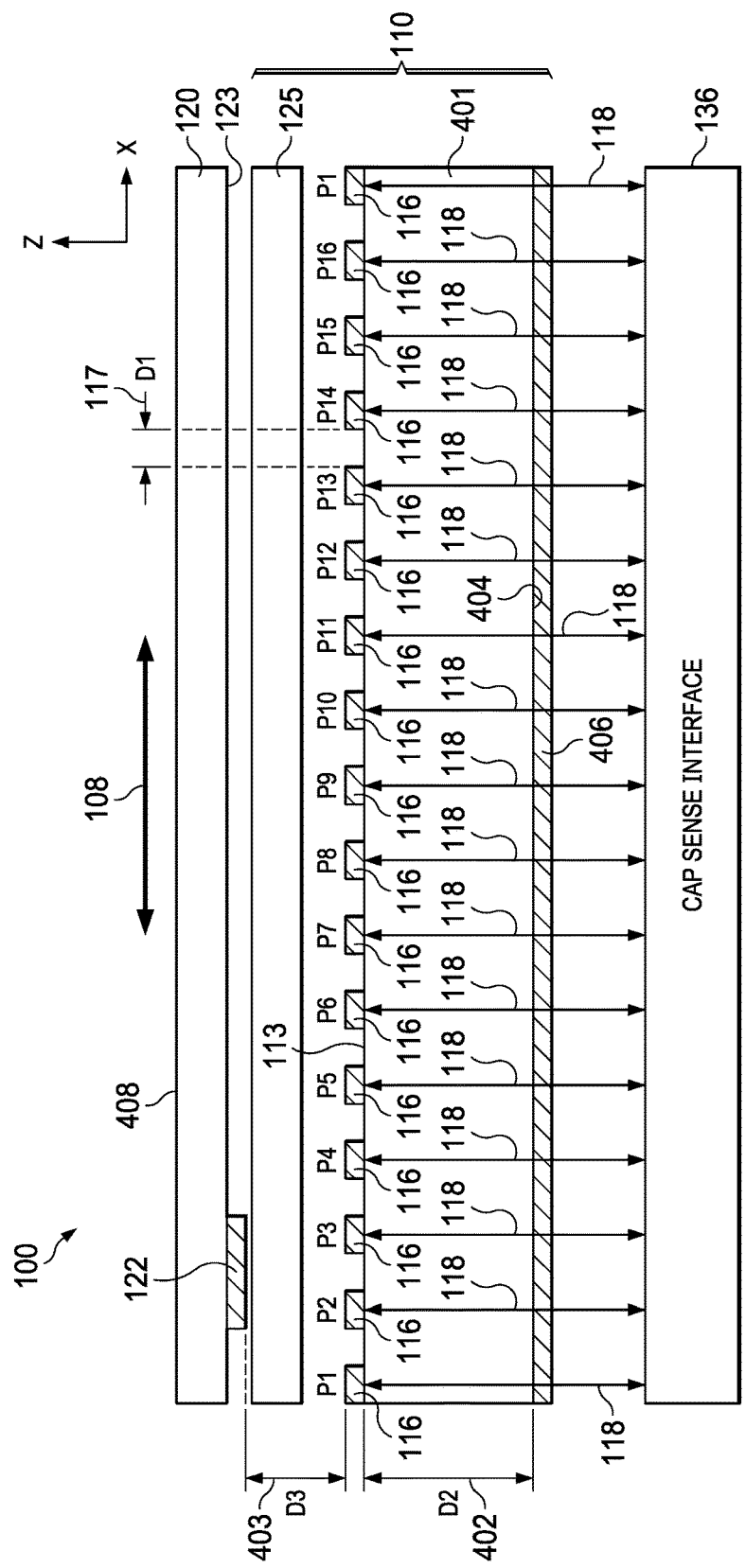
FIG. 15 is a partial sectional side elevation view taken along line 15-15 of the control apparatus of FIG. 14.

FIGS. 14 and 15 illustrate another possible implementation 100, in which the first direction 108 is linear. In this case, 17 structures 116 are linearly spaced from one another (labeled P1, P2, P3, P4, P5, P6, P7, P8, P9, P10, P11, P12, P13, P14, P15, P16, and a duplicate P1). FIG. 14 shows a top view and FIG. 15 shows a side view. The linear mechanical control apparatus 100 includes a stationary first structure 110 and a linearly translatable second user interface structure 120 for a user interface or HMI. The control apparatus 100 operates in generally similar fashion to the rotational apparatus 100 discussed above, with the second structure 120 translatable along a linear first direction 108 (along the X direction in FIGS. 14 and 15) relative to the stationary first structure 110. Like the apparatus 100 discussed above, the control apparatus 100 of FIGS. 14 and 15 can include both capacitive and optical linear position detection features, where the LEDs and reflectors are omitted in the illustrated example. The first structure 110 in FIG. 15 also includes a transparent protective overlay 125 with a bottom side that extends over the top surfaces of the conductive capacitor structures 116. The conductive capacitor plate structures 116 on the first side 113 form an integer number capacitors. The second structure 120 includes a bottom or second side 123 with a conductive structure 122 that faces the conductive capacitor plate structures 116 of the first structure 110. Depending on the position of the second structure 120, the conductive structure 122 selectively modifies the capacitance of a given one of the capacitor plate structures 116 when the conductive structure 122 is positioned proximate the given structure 116.

Figures 16, 17:
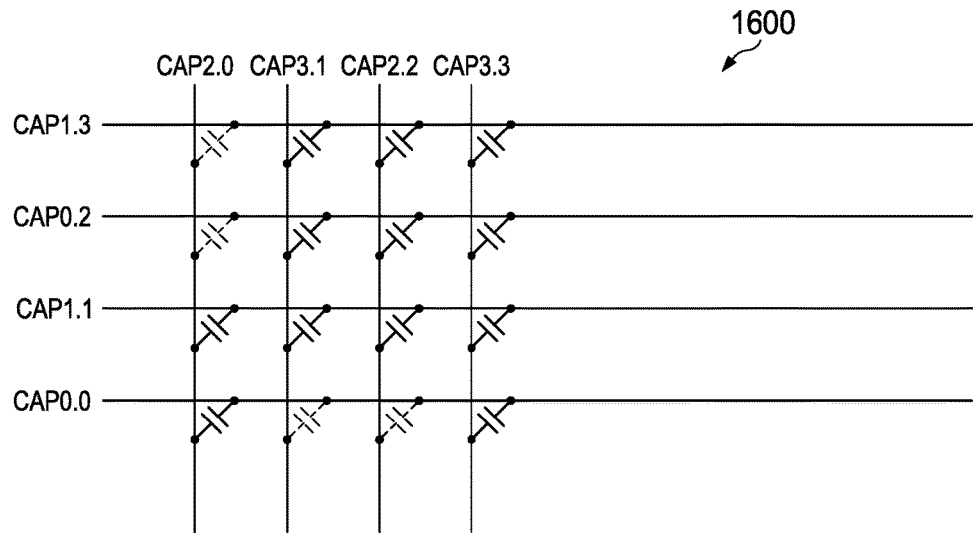
FIG. 16 is a schematic diagram of an example sensing configuration of conductive capacitor plate interconnections.
FIG. 17 is a table of an example position and user touch detection sequence in the apparatus of FIG. 1.

Referring now to FIGS. 16-19, in one example, the processor 132 uses matrix testing techniques to perform mutual and self-capacitance testing or measurements in the control apparatus 100. FIG. 16 shows an example sensing configuration 1600 including conductive capacitor plate interconnections. In this example, CAPx.y designates a multiplexer interconnection in an interface circuit 136 or in internal multiplexers of the MCU processor 132, using an integer number "x" multiplexers, each having "y" inputs. The individual multiplexers in certain examples are associated with a corresponding general-purpose I/O (GPIO).

Figure 18:
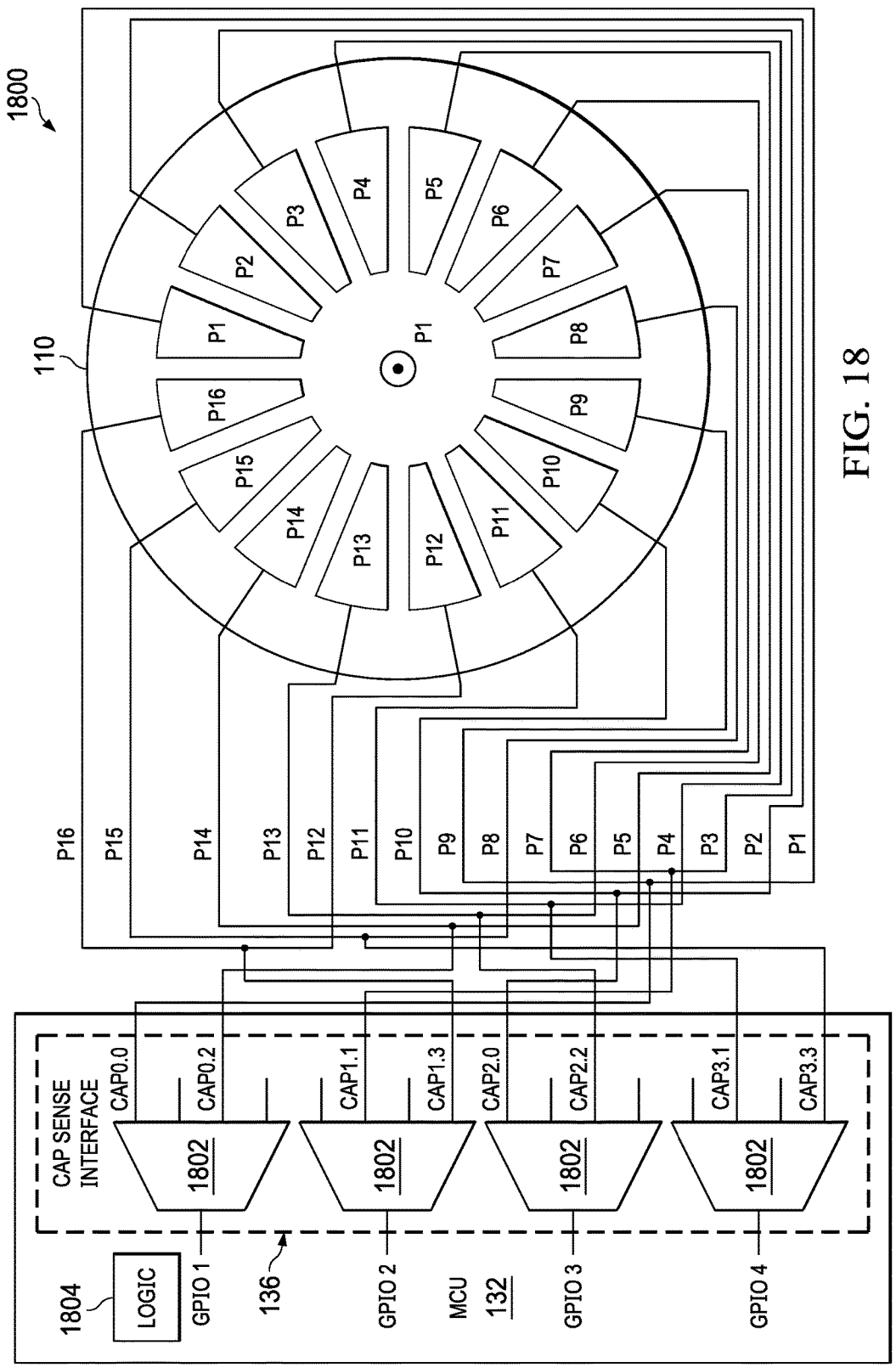
FIG. 18 is a partial schematic diagram of an example capacitive sense interface configuration with conductive capacitor plate interconnections for position and user touch detection using a reduced number of general purpose I/O connections in the apparatus of FIG. 1.
Figure 19:
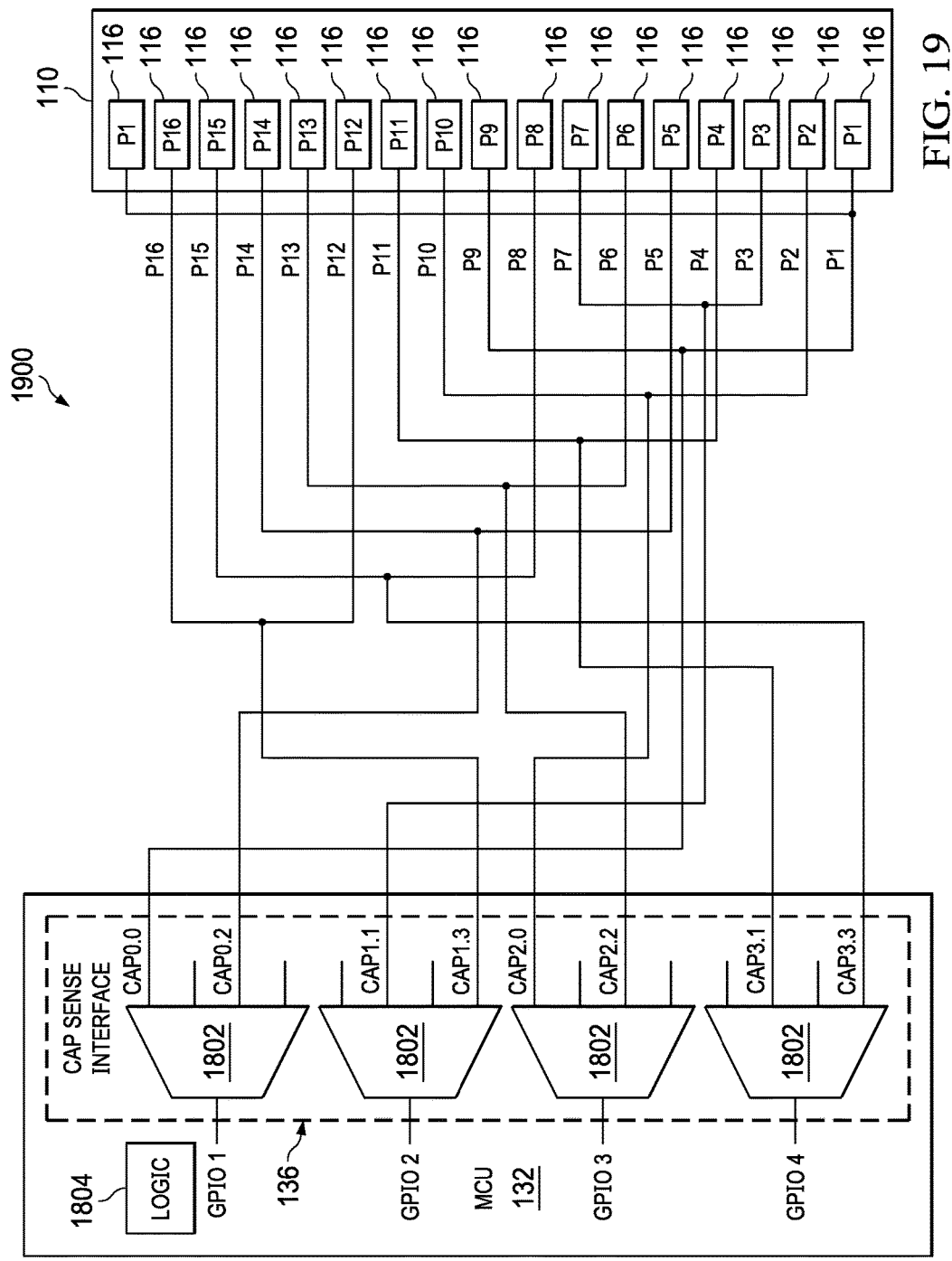
FIG. 19 is a partial schematic diagram of an example capacitive sense interface configuration with conductive capacitor plate interconnections for position and user touch detection using a limited number of general purpose I/O connections in the linear apparatus of FIGS. 14 and 15.

FIGS. 18 and 19 illustrate detailed examples for rotary and linear control apparatus examples 100, respectively, where "x" ranges from 0-3 and "y" ranges from 0-3. FIG. 17 shows a table 1700 that illustrates an example position and user touch detection truth table used in one example of the control apparatus 100, including 16 capacitor tests CT1-1, CT1-2, CT1-3, CT1-4, CT1-5, CT1-6, CT1-7, CT1-8, CT1-9, CT1-10, CT1-11, CT1-12, CT1-13, CT1-14, CT1-15 and CT1-16 indicated in a first column of the table 1700. The second column of the table shows interconnections for that particular test. For example, for detection of a touch event at position CT1-1 (P1), a capacitive response is expected in this example at a connection CAP1.3, a connection CAP0.0 and a connection CAP2.0. In one example, where the auxiliary conductive structure 122 and/or a user's finger is present, the maximum response is expected for this condition at the connection CAP0.0, and the signaling from the neighboring connections CAP1.3 and CAP2.0 exhibit lower but noticeable responses. For this particular test, the conductive capacitor plate structure 116 associated with CAP0.0 is the center or given (e.g., TX) electrode, and is tested along with its neighboring electrodes CAP1.3 and CAP2.0. In operation, the processor 132 sequentially performs the 16 tests for each of the mutual capacitance tests, and the first and second self-capacitance tests. FIG. 18 shows a configuration 1800 and includes the corresponding electrical connections 118 for the rotary implementation, in which the conductive capacitor plate structures 116 are sequentially labeled P1-P16 in a clockwise manner. In the first test CT1-1 in the table 1700 of FIG. 17, for example, the conductive capacitor plate structure 116 associated with CAP0.0 is labeled P1 in FIGS. 18 and 19. When this plate structure 116 is the given structure being tested, the structure 116 labeled P1 is the center or given (e.g., TX) electrode, and is tested along with its counterclockwise neighbor P16 (CAP1.3) and its clockwise neighbor P2 (CAP2.0). FIG. 19 illustrates a corresponding linear configuration interconnection example 1900. In order to facilitate the testing interconnection and operation for a given electrode and neighboring electrodes, the linear example 100 includes duplicate P1 electrodes 116 at opposite ends of the linear configuration.

Modifications are possible in the described embodiments, and other embodiments are possible, within the scope of the claims.

What is claimed is:

1. A control apparatus for a user interface, comprising:
   a first structure, including a plurality of conductive capacitor plate structures spaced from one another along a first direction on a first side of the first structure;
   a second structure movable relative to the first structure along the first direction, the second structure including a second side facing the first side of the first structure, and an auxiliary conductive structure positioned on the second side of the second structure to move along the first direction to selectively modify a capacitance associated with a given one of the conductive capacitor plate structures when the auxiliary conductive structure is positioned proximate the given one of the capacitor plate structures; and
   an interface circuit to provide excitation signals to the conductive capacitor plate structures and receive sense signals from the conductive capacitor plate structures to perform a mutual capacitance test of groups of the conductive capacitor plate structures and to perform a self-capacitance test of individual ones of the conductive capacitor plate structures to provide a position signal that represents a position of the second structure or a user's finger relative to a position of the first structure along the first direction according to signals from the conductive capacitor plate structures during one of the mutual capacitance test and the self-capacitance test.

2. The control apparatus of claim 1, wherein:
   the conductive capacitor plate structures are spaced from one another by a first distance along the first direction;
   the first structure further includes:
      a second side opposite to the first side; and
      a further conductive structure on the second side, the further conductive structure being spaced from the conductive capacitor plate structures by a second distance along a second direction; and
   the auxiliary conductive structure is spaced from the conductive capacitor plate structures by a third distance along the second direction.

3. The control apparatus of claim 2, wherein:
   the second distance is greater than the first distance; and
   the first distance is greater than the third distance.

4. The control apparatus of claim 3, wherein the interface circuit is configured to provide an excitation signal to the given one of the conductive capacitor plate structures and to receive a sense signal from a neighboring conductive capacitor plate structure to perform the mutual capacitance test of the groups of the conductive capacitor plate structures.

5. The control apparatus of claim 4, wherein the interface circuit is configured to provide the excitation signal to the given one of the conductive capacitor plate structures, receive a sense signal from the given one of the conductive capacitor plate structures, and control a voltage of the neighboring conductive capacitor plate structure to perform the self-capacitance test of the given one of the conductive capacitor plate structures.

6. The control apparatus of claim 5, wherein:
   the interface circuit is configured to provide the excitation signal to the given one of the conductive capacitor plate structures, receive the sense signal from the given one of the conductive capacitor plate structures, and set the voltage of the neighboring conductive capacitor plate structure to a first voltage value to perform a first self-capacitance test of the given one of the conductive capacitor plate structures; and
   the interface circuit is configured to provide the excitation signal to the given one of the conductive capacitor plate structures, receive the sense signal from the given one of the conductive capacitor plate structures, and allow the neighboring conductive capacitor plate structure to float to perform a second self-capacitance test of the given one of the conductive capacitor plate structures.

7. The control apparatus of claim 5, wherein:
   the interface circuit is configured to provide the excitation signal to the given one of the conductive capacitor plate structures, receive the sense signal from the given one of the conductive capacitor plate structures, and set the voltage of the neighboring conductive capacitor plate structure to a first voltage value to perform a first self-capacitance test of the given one of the conductive capacitor plate structures; and
   the interface circuit is configured to provide the excitation signal to the given one of the conductive capacitor plate structures, receive the sense signal from the given one of the conductive capacitor plate structures, and set the voltage of the neighboring conductive capacitor plate structure to a second voltage value to perform a second self-capacitance test of the given one of the conductive capacitor plate structures.

8. The control apparatus of claim 1, wherein the interface circuit is configured to provide an excitation signal to the given one of the conductive capacitor plate structures, receive a sense signal from the given one of the conductive capacitor plate structures, and control a voltage of a neighboring conductive capacitor plate structure to perform the self-capacitance test of the given one of the conductive capacitor plate structures.

9. The control apparatus of claim 8, wherein:
   the interface circuit is configured to provide the excitation signal to the given one of the conductive capacitor plate structures, receive the sense signal from the given one of the conductive capacitor plate structures, and set the voltage of the neighboring conductive capacitor plate structure to a first voltage value to perform a first self-capacitance test of the given one of the conductive capacitor plate structures; and
   the interface circuit is configured to provide the excitation signal to the given one of the conductive capacitor plate structures, receive the sense signal from the given one of the conductive capacitor plate structures, and allow the neighboring conductive capacitor plate structure to float to perform a second self-capacitance test of the given one of the conductive capacitor plate structures.

10. The control apparatus of claim 8, wherein:
   the interface circuit is configured to provide the excitation signal to the given one of the conductive capacitor plate structures, receive the sense signal from the given one of the conductive capacitor plate structures, and set the voltage of the neighboring conductive capacitor plate structure to a first voltage value to perform a first self-capacitance test of the given one of the conductive capacitor plate structures; and
   the interface circuit is configured to provide the excitation signal to the given one of the conductive capacitor plate structures, receive the sense signal from the given one of the conductive capacitor plate structures, and set the voltage of the neighboring conductive capacitor plate structure to a second voltage value to perform a second self-capacitance test of the given one of the conductive capacitor plate structures.

11. The control apparatus of claim 1, wherein the interface circuit is configured to provide an excitation signal to the given one of the conductive capacitor plate structures and to receive a sense signal from a neighboring conductive capacitor plate structure to perform the mutual capacitance test of the groups of the conductive capacitor plate structures.

12. The control apparatus of claim 1, wherein the first direction is circumferential relative to an axis.

13. The control apparatus of claim 1, wherein the first direction is linear.

14. The control apparatus of claim 1, further comprising:
an integer number N optical sources positioned on the first side of the first structure to selectively direct light away from the first side, N being greater than I;
an integer number N optical sensors positioned on the first side of the first structure to selectively sense light directed toward the first side of the first structure, individual optical sensors positioned proximate, the optical sources and optical sensors forming N optical device pairs spaced from one another along the first direction; and
a reflector positioned on the second side of the second structure to move along the first direction to selectively reflect light from one of the optical sources to the corresponding optical sensor of a given one of the optical device pairs when the reflector is positioned proximate the given one of the optical device pairs;
wherein the interface circuit is configured to provide the position signal according to signals from the optical sensors and signals from the conductive capacitor plate structures.

15. A control apparatus for a user interface, comprising:
a first structure, including a first side, a plurality of conductive capacitor plate structures spaced from one another by a first distance along a first direction on the first side, a second side opposite to the first side, and a further conductive structure on the second side of the first structure, the further conductive structure being spaced from the plurality of conductive capacitor plate structures by a second distance along a second direction;
a second structure movable relative to the first structure along the first direction, the second structure including a second side facing the first side of the first structure, and an auxiliary conductive structure positioned on the second side of the second structure to move along the first direction to selectively modify a capacitance associated with a given one of the plurality of conductive capacitor plate structures when the auxiliary conductive structure is positioned proximate the given one of the plurality of capacitor plate structures, the auxiliary conductive structure being spaced from the plurality of conductive capacitor plate structures by a third distance along the second direction; and
an interface circuit to provide excitation signals to the plurality of conductive capacitor plate structures and receive sense signals from the plurality of conductive capacitor plate structures to provide a position signal that represents a position of the second structure or a user's finger relative to a position of the first structure along the first direction according to signals from the plurality of conductive capacitor plate structures during a capacitance test;
wherein the second distance is greater than the first distance, and the first distance is greater than the third distance.

16. The control apparatus of claim 15, wherein the first direction is circumferential relative to an axis.

17. The control apparatus of claim 15, wherein the first direction is linear.

18. The control apparatus of claim 15, further comprising:
an integer number N optical sources positioned on the first side of the first structure to selectively direct light away from the first side, N being greater than I;
an integer number N optical sensors positioned on the first side of the first structure to selectively sense light directed toward the first side of the first structure, individual optical sensors positioned proximate a corresponding one of optical sources, the optical sources and optical sensors forming N optical device pairs spaced from one another along the first direction; and
a reflector positioned on the second side of the second structure to move along the first direction to selectively reflect light from one of the optical sources to the corresponding optical sensor of a given one of the optical device N pairs when the reflector is positioned proximate the given one of the N optical device pairs;
wherein the interface circuit is configured to provide the position signal according to signals from the optical sensors and signals from the plurality of conductive capacitor plate structures.

19. A method of detecting a relative position of a stationary first user interface structure and a user's finger or a second user interface structure movable relative to the stationary first user interface structure along a first direction, the stationary first user interface structure having a plurality of conductive capacitor plate structures spaced from one another along the first direction, the method comprising:
performing a mutual capacitance test for groups of the plurality of conductive capacitor plate structures, including providing an excitation signal to a given one of the plurality of conductive capacitor plate structures, receiving a sense signal from a neighboring conductive capacitor plate structure, and determining a mutual capacitance associated with the given one of the conductive capacitor plate structures according to the corresponding sense signal;
performing at least one self-capacitance test for individual ones of the plurality of conductive capacitor plate structures, including providing the excitation signal to the given one of the plurality of conductive capacitor plate structures, controlling a voltage of the neighboring conductive capacitor plate structure while providing the excitation signal to the given one of the plurality of conductive capacitor plate structures, receiving the sense signal from the given one of the plurality of conductive capacitor plate structures, and determining a self-capacitance associated with the given one of the plurality of conductive capacitor plate structures according to the corresponding sense signal; and
processing measured capacitances to identify the relative position of the stationary first user interface structure and the user's finger or the second user interface structure according to mutual capacitances and self-capacitances associated with the individual conductive capacitor plate structures.

20. The method of claim 19, further comprising:
performing a first self-capacitance test for the individual ones of the plurality of conductive capacitor plate structures, including providing the excitation signal to the given one of the plurality of conductive capacitor plate structures, setting the voltage of the neighboring conductive capacitor plate structure to a first voltage value while providing the excitation signal to the given one of the plurality of conductive capacitor plate structures, receiving the sense signal from the given one of the plurality of conductive capacitor plate structures, and determining a first self-capacitance associated with the given one of the plurality of conductive capacitor plate structures according to the corresponding sense signal;

performing a second self-capacitance test for the individual ones of the plurality of conductive capacitor plate structures, including providing the excitation signal to the given one of the plurality of conductive capacitor plate structures, setting the voltage of the neighboring conductive capacitor plate structure to a second voltage value or allowing the neighboring conductive capacitor plate structure to float while providing the excitation signal to the given one of the plurality of conductive capacitor plate structures, receiving the sense signal from the given one of the plurality of conductive capacitor plate structures, and determining a second self-capacitance associated with the given one of the conductive capacitor plate structures according to the corresponding sense signal; and processing measured capacitances to identify the relative position of the stationary first user interface structure and the user's finger or the second user interface structure according to mutual capacitances and the first and second self-capacitances associated with the individual of the plurality of conductive capacitor plate structures.

* * * * *